(12) United States Patent
Vitale et al.

(10) Patent No.: US 9,763,759 B2
(45) Date of Patent: Sep. 19, 2017

(54) APPARATUS AND METHODS FOR REDUCING FOAMING DURING SALIVA COLLECTION

(71) Applicant: Apnicure, Inc., Redwood City, CA (US)

(72) Inventors: Nicholas R. Vitale, Foster City, CA (US); Kenneth Mejia, San Francisco, CA (US); Michael C. Holzbaur, Menlo Park, CA (US); John Edwards Crowe, Menlo Park, CA (US); Jonathan L. Podmore, San Carlos, CA (US)

(73) Assignee: Apnicure, Inc., Redwood City, CA (US)

( * ) Notice: Subject to any disclaimer, the term of this patent is extended or adjusted under 35 U.S.C. 154(b) by 0 days.

(21) Appl. No.: 15/164,469

(22) Filed: May 25, 2016

(65) Prior Publication Data

US 2016/0262859 A1    Sep. 15, 2016

Related U.S. Application Data

(62) Division of application No. 13/546,453, filed on Jul. 11, 2012, now Pat. No. 9,375,541.

(51) Int. Cl.
*A61C 17/06* (2006.01)
*A61M 16/00* (2006.01)
(Continued)

(52) U.S. Cl.
CPC ............ *A61C 17/046* (2013.01); *A61F 5/566* (2013.01); *A61M 1/0001* (2013.01);
(Continued)

(58) Field of Classification Search
CPC .. A61C 17/0208; A61C 17/046; B01D 29/58; B01D 29/50; B01D 29/56;
(Continued)

(56) References Cited

U.S. PATENT DOCUMENTS 3,132,647 A    5/1964  Corniello
3,782,414 A *  1/1974  Holbrook ........... A61B 5/02042
                                                137/575

(Continued)

FOREIGN PATENT DOCUMENTS

KR    101035745 B1    5/2011
WO    WO-0025666 A1   5/2000

OTHER PUBLICATIONS

International search report and written opinion dated Oct. 17, 2013 for PCT/US13/049990.

(Continued)

*Primary Examiner* — Heidi M Eide
(74) *Attorney, Agent, or Firm* — Wilson, Sonsini, Goodrich & Rosati

(57) ABSTRACT

A saliva collector comprises a reservoir, a bubble barrier, and a membrane, where the bubble barrier and membrane are arranged in tandem on a flow path from an inlet to an outlet on the reservoir. Air aspirated from a patient's oral cavity enters the reservoir through the inlet, passes through the bubble barrier to remove foam and bubbles, passes through the membrane to remove entrained liquid saliva, and passes out through the outlet.

20 Claims, 5 Drawing Sheets

(51) Int. Cl.
*A61M 1/00* (2006.01)
*A61F 5/56* (2006.01)
*A61M 16/04* (2006.01)

(52) U.S. Cl.
CPC .......... *A61M 16/00* (2013.01); *A61M 16/049* (2014.02); *A61M 16/0463* (2013.01)

(58) Field of Classification Search
CPC B01D 2221/10; B01D 36/001; B01D 36/003; A61M 16/049; A61M 16/0463; A61M 1/0001; A61M 16/00; A61F 5/566
See application file for complete search history.

(56) References Cited

U.S. PATENT DOCUMENTS

| | | | |
|---|---|---|---|
| 4,169,473 A | 10/1979 | Samelson | |
| 4,275,732 A * | 6/1981 | Gereg | A61M 1/0001 128/DIG. 24 |
| 4,304,227 A | 12/1981 | Samelson | |
| 4,655,754 A * | 4/1987 | Richmond | A61M 1/0056 137/197 |
| 4,676,240 A | 6/1987 | Gardy | |
| 4,806,135 A * | 2/1989 | Siposs | A61M 1/3627 210/304 |
| 4,834,110 A | 5/1989 | Richard | |
| 5,465,734 A | 11/1995 | Alvarez et al. | |
| 5,591,251 A | 1/1997 | Brugger | |
| 5,687,777 A * | 11/1997 | Dobson | A61M 16/183 141/18 |
| 5,957,133 A | 9/1999 | Hart | |
| 6,379,149 B1 | 4/2002 | Franetzki | |
| 6,467,484 B1 | 10/2002 | De Voss | |
| 6,494,209 B2 | 12/2002 | Kulick | |
| 6,877,513 B2 | 4/2005 | Scarberry et al. | |
| 6,955,172 B2 | 10/2005 | Nelson et al. | |
| 7,073,505 B2 | 7/2006 | Nelson et al. | |
| 7,073,506 B2 | 7/2006 | Robertson et al. | |
| 7,100,461 B2 * | 9/2006 | Bradley | G01N 1/02 73/864.33 |
| 7,153,294 B1 * | 12/2006 | Farrow | A61M 1/0001 604/317 |
| 7,182,082 B2 | 2/2007 | Hoffrichter | |
| 7,947,007 B2 | 5/2011 | Nakayama et al. | |
| 9,375,541 B2 | 6/2016 | Vitale et al. | |
| 2002/0127143 A1 * | 9/2002 | Kuo | A61B 10/0051 422/68.1 |
| 2004/0222141 A1 * | 11/2004 | Gray | A61C 17/046 210/300 |
| 2005/0166928 A1 | 8/2005 | Jiang | |
| 2005/0166929 A1 | 8/2005 | Jiang | |
| 2007/0277818 A1 | 12/2007 | Chen | |
| 2008/0188947 A1 | 8/2008 | Sanders | |
| 2008/0210244 A1 | 9/2008 | Keropian | |
| 2008/0216843 A1 | 9/2008 | Jiang | |
| 2009/0123886 A1 | 5/2009 | Vaska | |
| 2012/0132216 A1 | 5/2012 | Vaska | |
| 2012/0199135 A1 | 8/2012 | Podmore et al. | |

OTHER PUBLICATIONS

Notice of allowance dated Mar. 9, 2016 for U.S. Appl. No. 13/546,453.
Office action dated Apr. 20, 2015 for U.S. Appl. No. 13/546,453.
Office action dated May 12, 2014 for U.S. Appl. No. 13/546,453.
Office action dated Aug. 7, 2014 for U.S. Appl. No. 13/546,453.
Office action dated Sep. 2, 2015 for U.S. Appl. No. 13/546,453.

* cited by examiner

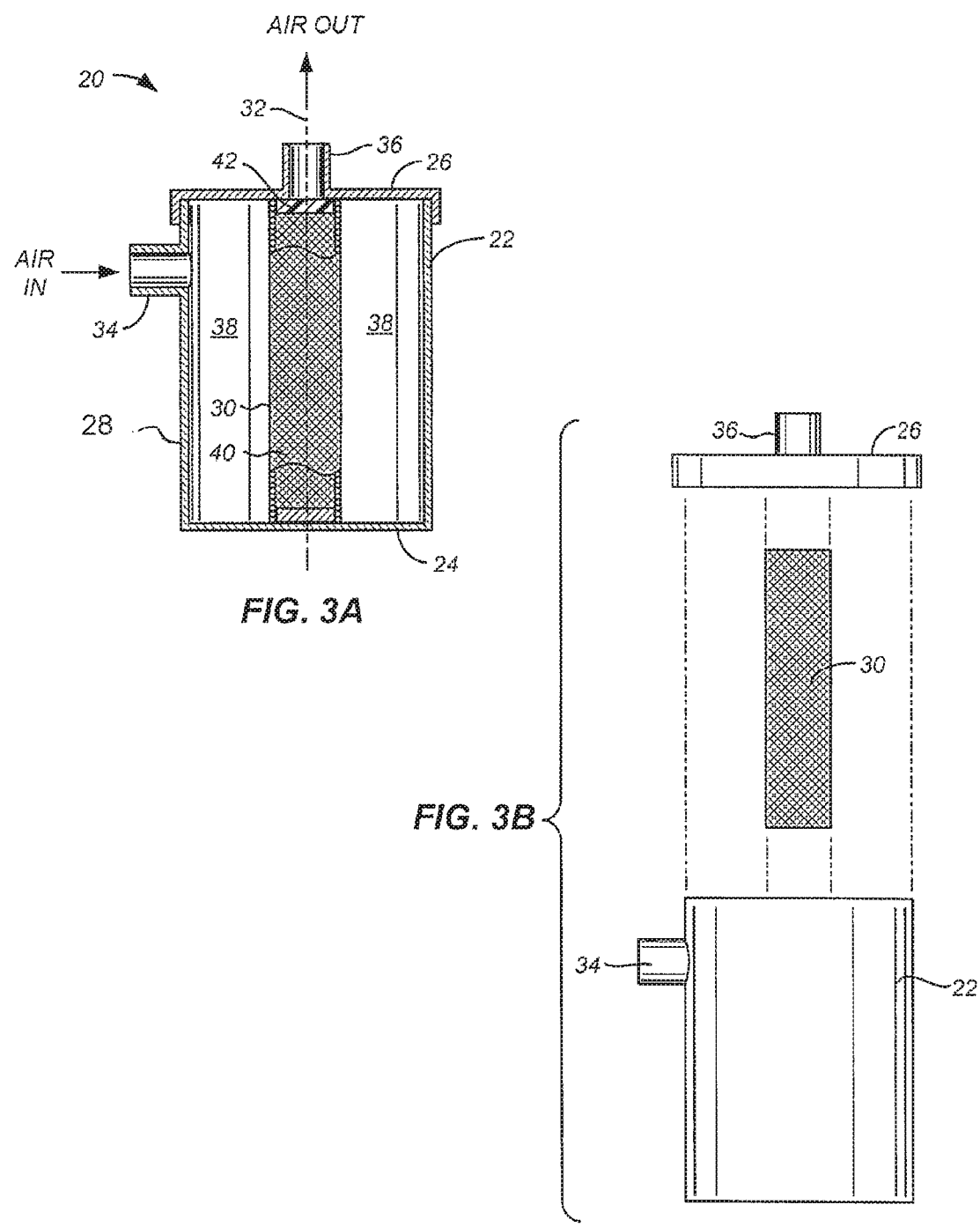

APPARATUS AND METHODS FOR REDUCING FOAMING DURING SALIVA COLLECTION

CROSS-REFERENCE

This application is a divisional application of U.S. patent application Ser. No. 13/546,453, filed Jul. 11, 2012, which is incorporated herein by reference in its entirety, and to which application we claim priority under 35 USC §121.

BACKGROUND OF THE INVENTION

1. Field of the Invention

The present invention relates generally to medical devices and methods. In particular, the present invention relates to a reservoir and methods for its use for the collection of saliva with a reduction in bubbling and foaming.

A vacuum may be applied to an appliance or device held in a patient's oral cavity for a variety of purposes. For example, an appliance for treating obstructive sleep apnea (OSA) may utilize a device held in a patient's mouth where a vacuum is constantly drawn on the device in order to reposition portions of the patient's oral anatomy to reduce the likelihood of OSA. The device may be used for or in conjunction with drawing a patient's tongue and/or lower mandible forward in order to reduce OSA. Of particular interest to the present invention, the vacuum may be drawn in order to help draw the soft palate and/or rear portion of a patient's tongue away from the pharynx in order to maintain a clear breathing passage.

In all such devices which draw a partial negative pressure within the oral cavity, there is a likelihood that a flow of saliva will be created in tubes and other flow passages connected to the oral appliance to maintain the vacuum. In order to avoid fouling the equipment which produces the vacuum, a saliva collector may be provided in-line to remove and collect the saliva.

FIG. 1 is taken from FIG. 25 of co-pending, commonly owned U.S. Patent Publication No. 2012/0132216, the full disclosure of which is incorporated herein by reference. FIG. 1 illustrates a system 489 including an oral device 490, a vacuum pump 492, a saliva reservoir 494, and a pressure sensor 496. Oral device 490 further includes a pressure conduit 498 extending through bite structure 500 to the superior side of tongue constraint 502 where pressure conduit 498 has a distal opening 504. The pressure conduit 498 may alternatively comprise an inner lumen formed integrally within tongue constraint 502 or bite structure 500, and distal opening 504 could be positioned in any of various positions relative to bite structure 500 as may be desired to measure pressure within the oral cavity. A vacuum lumen 506 extends from the superior surface of tongue constraint 502 through bite structure 500 and both vacuum lumen 506 and pressure conduit 498 extend through lip seal 508. Vacuum lumen 506 is connected to a vacuum tube 510 which connects in an airtight manner to an input fitting 512 on saliva reservoir 494. Vacuum tube 510 has a vent hole 511 anterior to lip seal 508 so as to be outside the patient's oral cavity but positioned as close to oral device 490 as practicable while minimizing risk of obstruction by the patient's lips or other tissues. Alternatively vent hole 511 may be disposed in vacuum lumen 506 anterior to bite structure 500 or on the superior side of tongue constraint 502 so as to be located within the patient's oral cavity. When a negative pressure (partial vacuum) is applied through vacuum lumen 506 within the patient's oral cavity, saliva or other liquids which collect may be aspirated through vacuum lumen 506 and vacuum tube 510. While removing excess liquids from the oral cavity is desirable, the weight of the liquid within vacuum tube 510 may create a pressure offset in vacuum tube 510 which would then affect the negative pressure applied within the oral cavity. System 489 alleviates this problem by providing vent hole 511 in vacuum tube 510, allowing any aspirated liquids to flow to saliva reservoir 494 more quickly.

While effective, the saliva collection system described above can result in the mixing of air and saliva in the vacuum flow path which in turn will create bubbles and foam inside of the reservoir. In some cases, it is possible for the bubbles and foam to accumulate so that they reach the outlet fitting 516 connected to vacuum pump 492, as illustrated in FIG. 1. Even if the foaming does not reach that level, handling and/or accidental disturbance of the reservoir in such systems can allow saliva to enter the vacuum tubing leading to the vacuum pump.

For these reasons, it would be desirable to provide alternative and improved methods and apparatus for removing and collecting saliva in vacuum systems used with oral appliances and other devices. The methods and devices should be effective in cases of even the most excessive bubbling and foaming as well as in cases where the reservoir may be completely inverted. Such methods and systems should be simple and inexpensive to implement. At least some of these objectives will be met by the inventions described hereinafter.

2. Description of the Background Art

U.S. Patent Publication No. 2012/0132216 has been described above. U.S. Ser. No. 13/023,763, the full disclosure of which is incorporated herein by reference, is another co-pending, commonly owned U.S. Patent Application, filed on Feb. 9, 2011, and describes an alternative saliva management system of oral appliances. Oral and external devices for treating sleep apnea and snoring are described in U.S. Patent Publication Nos. US2005/166929; US2005/166928; US2008/0188947; US2007/0277818; US2008/0216843; and US2008/0210244; and in U.S. Pat. Nos. 7,182,082; 7,073,506; 7,073,505; 6,955,172; 6,877,513; 6,494,209; 5,957,133; 5,465,734; 4,676,240; 4,304,227; 4,169,473; and 3,132,647.

SUMMARY OF THE INVENTION

The present invention provides apparatus and methods for the improved collection of saliva from aspirated air streams entrained with saliva, typically originating from a patient's oral cavity. In particular, the present invention provides for collecting saliva with reduced or eliminated formation of bubbles and foam in a collection reservoir. As described above, use of a vacuum to aspirate air from a patient's oral cavity can result in entrained saliva which should be removed before the aspirated air stream reaches a vacuum pump or other vacuum source. While a simple collection reservoir may be placed in a vacuum line from the oral cavity before the pump, as described in U.S. Patent Publication No. 2012/0132216, where the majority of saliva will drop to the bottom of the collection reservoir, excessive bubbles and foaming can result in loss of saliva through an outlet port on the reservoir, thus risking saliva reaching the vacuum pump or other vacuum source.

While the passage of saliva bubbles and foam through the outlet port might be overcome by a simple membrane or other barrier placed over the outlet port, it has been found by the inventors herein that such a simple barrier can itself become fouled over time which can interfere with operation of the vacuum system. Thus, even if saliva is inhibited from leaking from the reservoir, operation of the vacuum system may still be impaired.

The present invention provides for further improvement in saliva collection reservoirs and methods by placing a bubble barrier alone or more usually in tandem with a membrane along an air flow path from the oral device to the vacuum or other source. In particular, a first barrier, referred to hereinafter as a "bubble barrier," acts to remove or suppress the formation of bubbles and foam. By placing the bubble barrier a sufficient distance from the reservoir outlet, in some instances an acceptable amount of saliva can be removed and no further barrier is needed. Usually, though, after passing through the bubble barrier, the pre-treated air stream reaches a second barrier, typically a membrane barrier, that removes still-entrained liquid saliva from the air stream before reaching the pump. The saliva resulting from the suppression of bubbles and foam as well as that removed by the second barrier is collected at the bottom of the reservoir together with that saliva which has separated upon entry into the reservoir.

In a first aspect of the present invention, a saliva collector for attachment in a vacuum line which aspirates an air stream entrained with saliva comprises a reservoir, a bubble barrier, and a membrane. The reservoir has a bottom, a top, and a sidewall which together define an interior volume. The reservoir further has an air inlet and an air outlet with an air flow path therebetween. The bubble barrier is positioned within the interior of the reservoir so that all air on the flow path passes through the bubble barrier. The bubble barrier is spaced apart from the outlet and disrupts bubbles and foam present in the air stream before such bubbles and foam can reach the outlet or membrane. The disrupted bubbles and foam typically coalesce back into liquid saliva which falls to the bottom of the reservoir and is collected together with saliva which has separated by gravity upon entry into the reservoir. The pre-treated air stream passing from the bubble barrier will usually next pass through the membrane which is positioned downstream on the flow path. Most or all of the pre-treated air will pass through the membrane, and the membrane allows the air to pass with minimal restriction while preventing passage of liquid saliva, so that a fully treated air stream passes out from the reservoir through the outlet port. In this way, liquid saliva is effectively prevented from reaching any downstream vacuum pump or other vacuum source. The membranes which are commonly employed may allow some water vapor to pass, but some membranes may block some or all water vapor as well.

The bubble barrier may have a variety of different configurations. Typically, the bubble barrier will be a perforate barrier, such as a plate, sheet, or film having discrete holes or perforations there through, typically having openings with an area from about 0.5 mm$^2$ to 2 mm$^2$. Alternatively, the bubble barrier could be in the form of a mesh, screen, or other woven or similar structure comprising discrete elements. Such barriers will function by physically disrupting the bubbles and foam so that the surface tension is broken and the bubbles and foam coalesce into liquid which will drop and separate by gravity to collect at the bottom of the reservoir. In alternative embodiments, the bubble barrier could be in the form of a single or multiple funnel-shaped inlets which again physically interact with the bubbles and foam to reduce surface tension. Still further alternatively, the bubble barrier could comprise one or more heated wires, optionally in the form of a mesh, which can interact to disrupt the bubbles and foam.

In the exemplary embodiments, the bubble barrier will be a cylindrical mesh or perforated wall which is arranged axially within the reservoir to define an outer annular region for receiving the airflow from the patient's oral cavity and an inner region which allows fluid collection and flow of the pre-treated air from which the bubbles and foam have been removed. The use of such a vertical, cylindrical barrier is advantageous since it maximizes the area available to disrupt the foam and bubbles and is least affected by a rising level of the saliva as it collects on the bottom of the reservoir.

The saliva removal membrane will typically have both hydrophobic and oleophobic properties with an airflow resistance below about 40 cmH$_2$O at a flow rate of 120 ml/min. Typical barriers will be thin polymeric sheets of materials, such as polyvinylidene fluoride (PVDF), polytetrafluoroethylene (PTFE), polyethersulfone (PES), optionally coated to enhance oleophobicity to hydrophobic materials or to enhance hydrophobicity in hydrophilic materials.

In the exemplary embodiments, where the bubble barrier is a cylinder, the outer side wall of the reservoir will preferably also be cylindrical, thus forming an outer annular region within the reservoir for receiving the untreated air and an inner cylindrical region for allowing the pre-treated air to flow upwardly to the barrier and the outlet port. In exemplary embodiments, the reservoir will have a volume in the range from about 10 cm$^3$ to 1000 cm$^3$, and the bubble barrier will have a surface area of 20 cm$^2$ to 200 cm$^2$.

Exemplary embodiments of the present invention will further comprise inlet and outlet valves at the inlet and outlet of the reservoir, respectively. The valves will typically be self-opening valves which open when a line or fitting are connected to the reservoir for use and which close when the line or fitting is removed. In this way, the reservoir can be conveniently removed from the system while minimizing the risk that the collected saliva will be unintentionally spilled.

In a second aspect of the present invention, a method for removing saliva from an air stream aspirated from a patient's oral cavity comprises directing the air stream through a reservoir from an inlet, along a flow path, and to an outlet. The air stream is typically drawn by a partial vacuum applied at the outlet, typically a vacuum in the range from 2 cm H$_2$O to 250 cm H$_2$O, and the vacuum will typically cause bubbles and foam to form in the air stream as it enters the reservoir. After entering the reservoir, the air stream is passed through a bubble barrier to disrupt the bubbles and foam, thus providing a pre-treated air stream. The pre-treated air stream is then usually passed through a membrane to separate entrained liquid saliva to provide a treated air stream. The pre-treated air stream passes through the membrane after passing through the bubble barrier and before passing out through the outlet as the treated air stream.

In exemplary embodiments, the air stream originates from an oral appliance held in the patient's oral cavity, where the oral appliance is connected to the inlet of the reservoir by tubing.

In other preferred aspects, the nature of the bubble barrier and of the barrier membrane will be the same as those described above in connection with the apparatus of the present invention.

In further aspects of the methods of the present invention, the flow rate of the air stream will typically be in the range from 20 ml/min to 1000 ml/min. Other methods may further comprise disconnecting the reservoir from inlet and outlet conduits, draining collected saliva, cleaning the perforated barrier and membranes, and reconnecting the reservoir to the inlet and outlet conduits.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIGS. 3A and 3B are schematic illustrations of the first saliva collection reservoir system of the present invention.

DETAILED DESCRIPTION OF THE INVENTION

Figure 1:
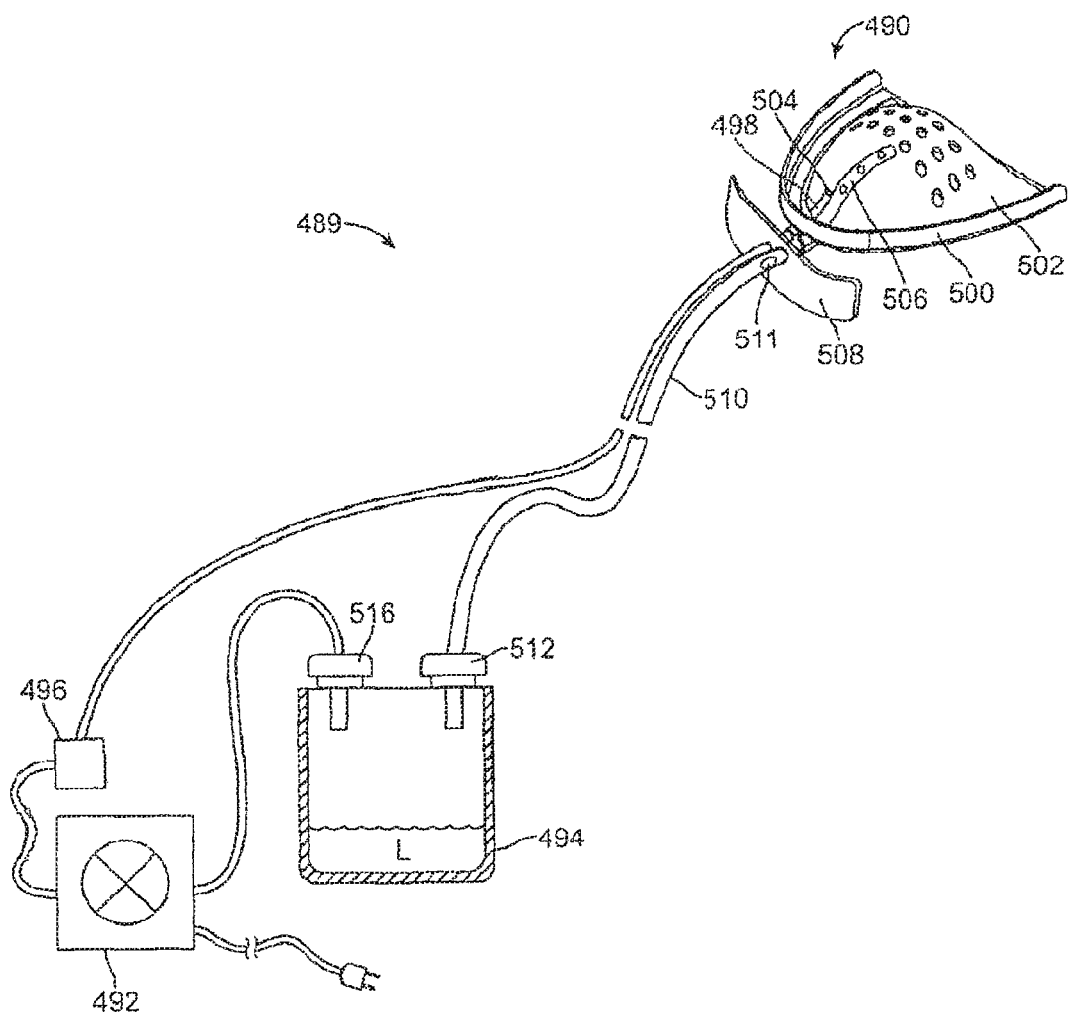
FIG. 1 illustrates a prior art system as found in U.S. Patent Application No. 2012-0132216.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The saliva collectors and reservoirs of the present invention may be used in a variety of systems, typically systems where a vacuum line is being used to withdraw an air stream from a patient's oral cavity. Exemplary of such systems is system 489 illustrated in FIG. 1 where the reservoirs of the present invention might be used in place of conventional saliva reservoir 494.

Figure 2:
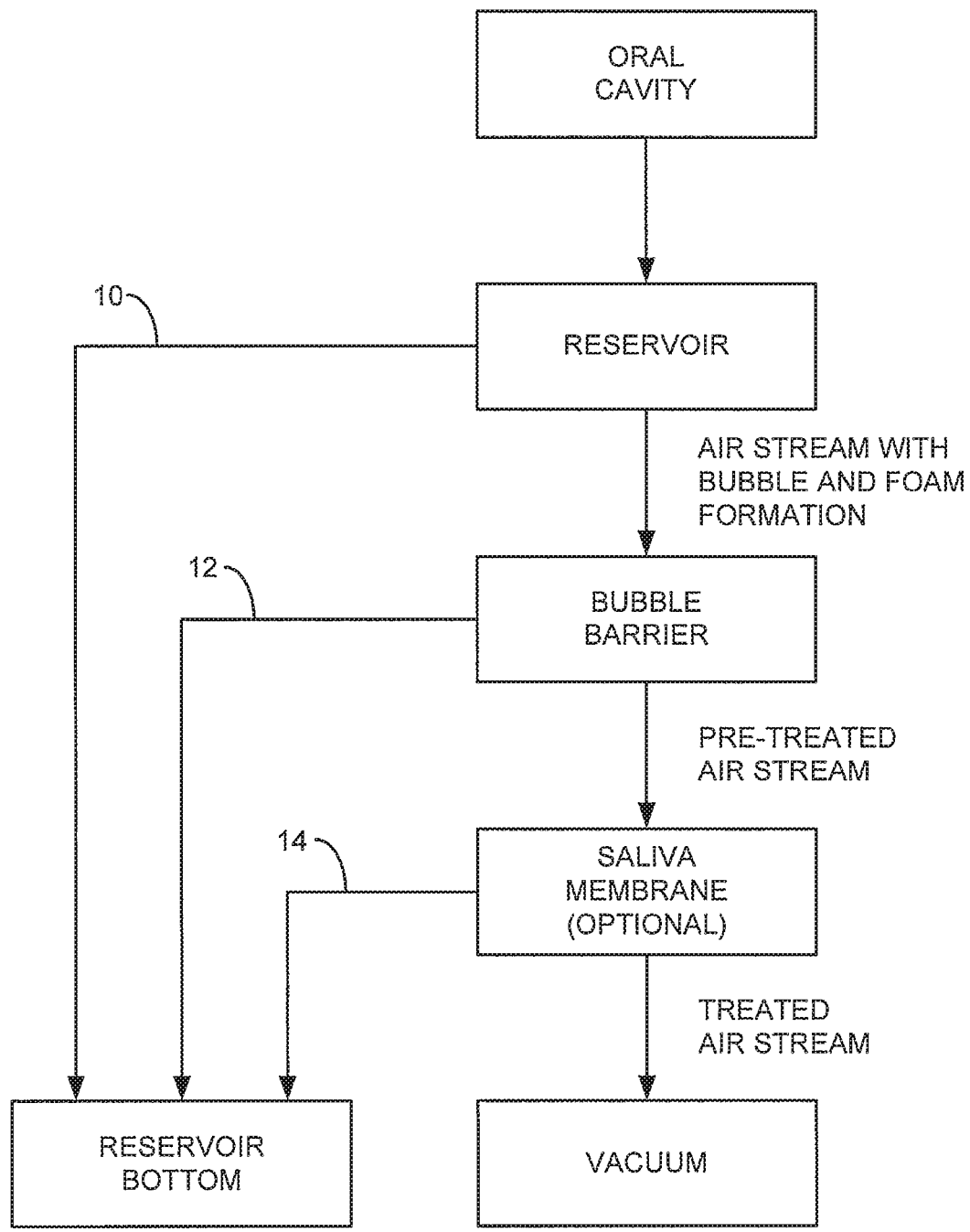
FIG. 2 is a flow chart illustrating the air stream flow and treatment steps of the methods of the present invention.

Referring to FIG. 2, the apparatus and methods of the present invention provide for drawing an air stream from an oral cavity using a vacuum source, such as a pump. The air stream first passes into a reservoir where a first volume 10 of saliva separates by gravity and falls to the reservoir bottom. The remaining air stream will typically have entrained bubbles and saliva foam which is to be removed before the air stream reaches a saliva membrane to remove entrained liquid saliva. The removal of the bubbles and foam is accomplished with a bubble barrier to produce a pre-treated air stream which is then directed through the saliva membrane. The treated air stream leaving the saliva membrane will then be directed out of the reservoir and flow directly or indirectly to the vacuum pump or other source. A quantity or volume 12 of liquid saliva resulting from disruption of the bubbles and foam by the bubble barrier will also drop to the reservoir bottom as will a third volume or quantity of 14 of liquid saliva which is produced by the saliva membrane.

Figure 4A:
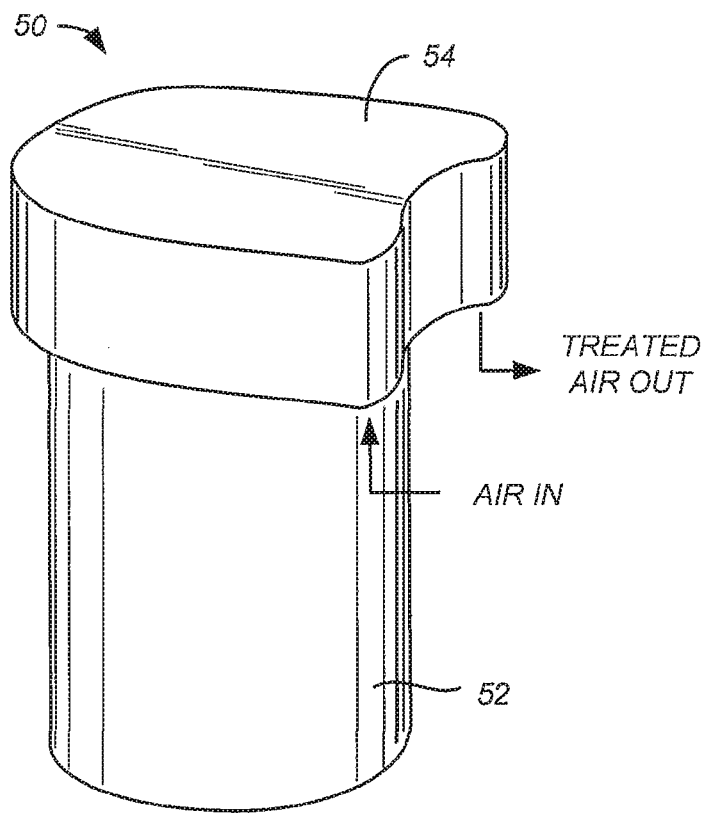
FIGS. 4A and 4B illustrate a more detailed second saliva collection reservoir system of the present invention.
Figure 4B:
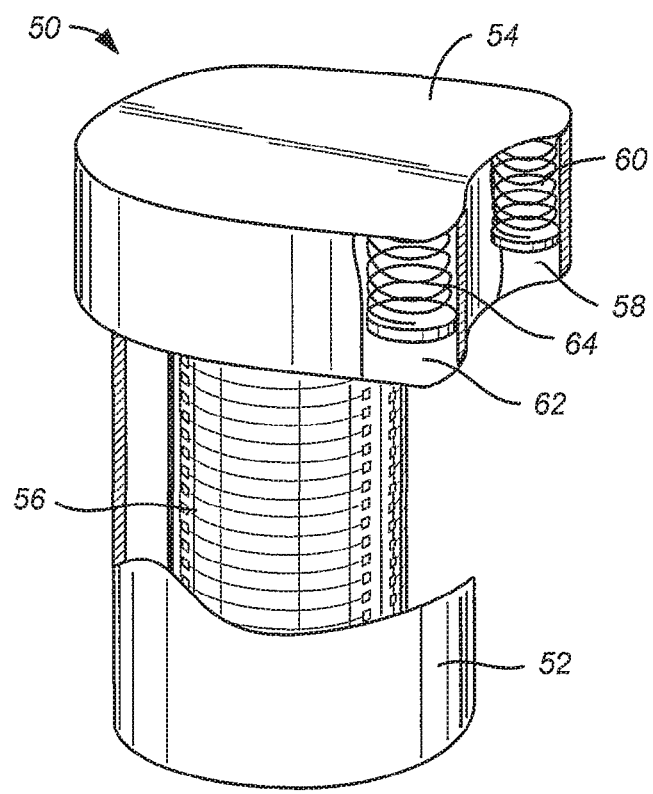

Referring to FIGS. 3 and 3B, a saliva collection reservoir 20 constructed in accordance with the principles of the present invention will include a reservoir enclosure 22 having a bottom 24, a removable top 26, and a cylindrical side wall 28. A bubble barrier 30, in the form of a cylindrical mesh or perforated wall, is aligned centrally along a vertical axis 32 of the reservoir body 22. An inlet port 34 is provided in the side wall of the body 22, typically near the top, and an outlet port 36 is formed centrally in the removable top 26 so that it is coaxially aligned with axis 32. In this way, an interior of the reservoir body 22 is divided into an outer, annular volume 38 and an inner cylindrical volume 40 (located within the cylindrical bubble barrier 30). Thus, air having entrained liquid saliva, foam, and bubbles entering through inlet port 34 will first enter and circulate around the annular volume 38 where liquid saliva will be able to separate and drop to the bottom of the reservoir. Before entering the inner cylindrical volume 40, however, the air will have to pass through the perforations of the bubble barrier 30, where the perforations will disrupt foam and bubbles which may be present. The foam and bubbles will be physically disrupted so that they coalesce and return to the liquid state, separate, and fall to the bottom of the reservoir. The pre-treated air stream which flows from the bubble barrier 30 into the inner cylindrical volume 40 will thus be free of entrained bubbles and foam, but will still have entrained liquid saliva which will be carried to the saliva membrane 42 before the air can exit through outlet 436. The saliva membrane 42 will separate the liquid saliva before the saliva can reach the vacuum pump. FIG. 3B shows the components of the saliva collection reservoir 20 in an exploded view. Referring now to FIGS. 4A and 4B, a second embodiment of a saliva collection reservoir 50 will be described. The saliva collection reservoir 50 includes the same basic components as reservoir 20, but further includes inlets and outlets having self-opening and closing valves so that the reservoir may be removed from a vacuum line with reduced risk of spillage.

The saliva collection reservoir 50 includes a cylindrical canister 52 and a removable top 54. A cylindrical perforate barrier 56 is axially aligned within the anterior of the cylindrical canister 52, and an outlet 58 having an outlet valve 60 and an inlet 62 having an inlet valve 64 are disposed in the removable top 54.

Figure 5:
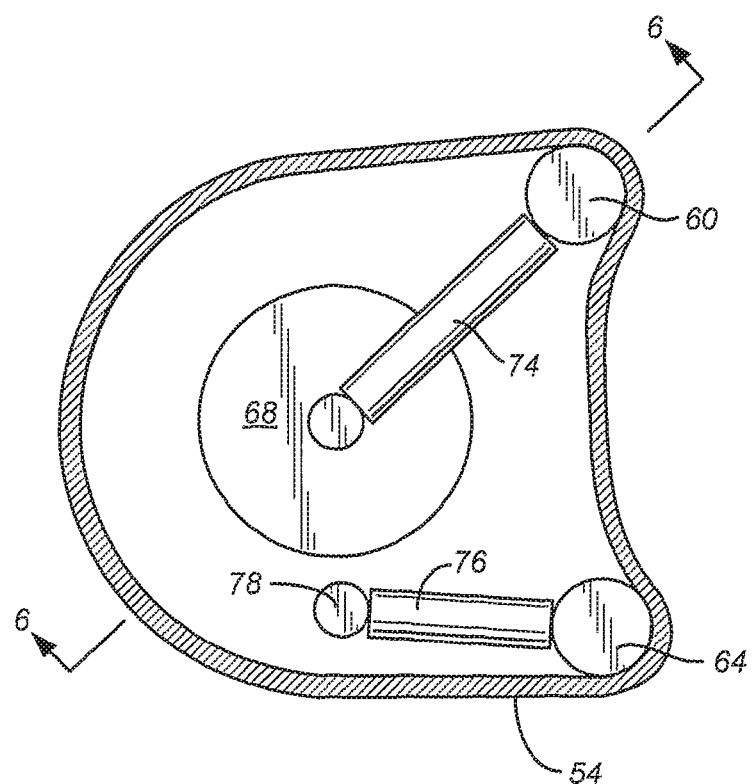
FIG. 5 is a top plan view of a portion of the saliva collection reservoir of FIGS. 4A and 4B.
Figure 6:
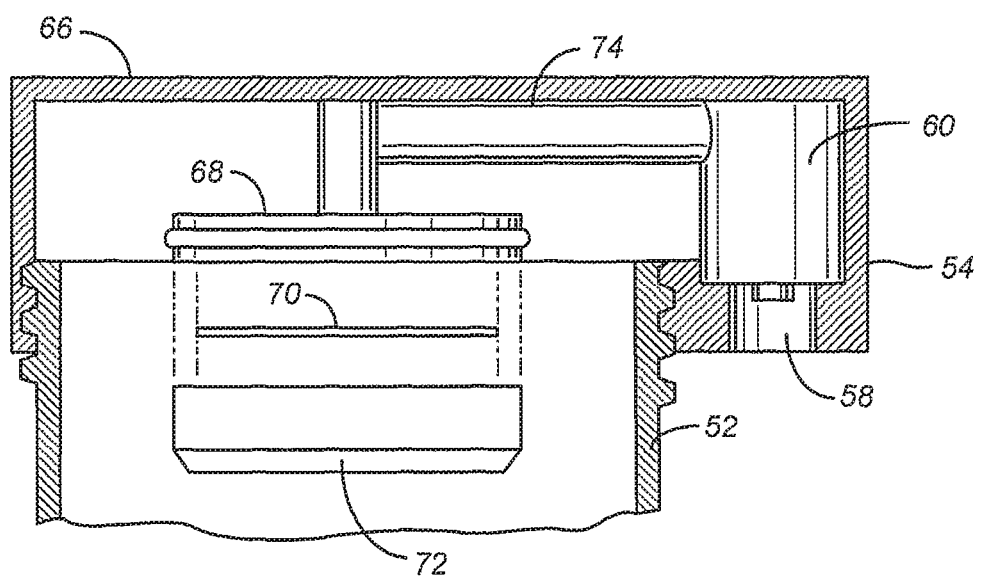
FIG. 6 is a cross-sectional view taken along line 6-6 of FIG. 5.

More detailed construction of the interior of the saliva collection reservoir 50 and of the flow paths therein are seen in FIGS. 5 and 6. FIG. 5 is a plan view of removable top 54 with the very top plate 66 (FIG. 6) removed. A fitting 68 attached within the removable top 54 receives the saliva membrane 70, which is held in place by a retaining ring 72. The retaining ring engages the cylindrical perforated barrier (FIG. 4B), so that the pre-treated air stream flows upwardly through the barrier into fitting 68 and then radially outwardly through tube 74 to the valve 60 and outlet 58. As best seen in FIG. 5, the inlet air passes in through valve 64, and inwardly through connecting tube 76, and then to a port 78, which passes the inlet air stream into the outer annular volume of the cylindrical canister 52.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A saliva collector for attachment in a vacuum line which aspirates an air stream entrained with saliva, said saliva collector comprising:

a reservoir having a bottom, a top, and a sidewall which together define an interior volume, said reservoir further having an air inlet and an air outlet with an air flow path between the air inlet and the air outlet; and a bubble barrier positioned within the interior of the reservoir so that all air on the flow path passes therethrough, wherein the bubble barrier is positioned within the interior of the reservoir to separate the reservoir into an inner portion and an outer portion, the bubble barrier extending to the bottom of the reservoir and the air flow path crossing the inner and outer portions, wherein the bubble barrier is cylindrical with the axial lumen aligned with the air inlet or the air outlet, and wherein the bubble barrier is configured to disrupt bubbles and foam present in the air stream before such bubbles of foam can reach the air outlet such that the bubbles and foam coalesce and return to a liquid state to fall to the bottom of the reservoir away from the air inlet and the air outlet.

2. A saliva collector as in claim 1, further comprising a membrane positioned within the interior of the reservoir on the flow path downstream of the bubble barrier so that all air passes therethrough before passing through the air outlet, wherein the membrane permits the flow of air but blocks the passage of saliva.

3. A saliva collector as in claim 2, wherein the membrane has both hydrophobic and oleophobic properties with an air flow resistance less than 40 cmH$^2$O at an airflow rate of 120 ml/min.

4. A saliva collector as in claim 3, wherein the membrane is composed of a material selected from the group consisting of polyvinylidene fluoride (PVDF), polytetrafluoroethylene (PTFE), polyethersulfone (PES), optionally coated to enhance oleophobicity to hydrophobic materials or to enhance hydrophobicity in hydrophilic materials.

5. A saliva collector as in claim 1, wherein the bubble barrier comprises a perforate barrier.

6. A saliva collector as in claim 5, wherein the reservoir has a volume in the range from 10 cm$^3$ to 1000 cm$^3$ and the perforate barrier has an area in the range from 20 cm$^2$ to 200 cm$^2$.

7. A saliva collector as in claim 1, wherein the bubble barrier comprises a mesh.

8. A saliva collector as in claim 7, wherein the cylindrical mesh has openings with an area from 0.5 mm$^2$ to 2 mm$^2$.

9. A saliva collector as in claim 1, wherein the sidewall is cylindrical.

10. A saliva collector as in claim 1, further comprising an inlet valve at the air inlet and an outlet valve at the air outlet, wherein the valves each open when connected to a conduit and close when disconnected from a conduit.

11. A saliva collector as in claim 10, wherein the valves are self-opening and closing.

12. A saliva collector as in claim 1, wherein the air flow path travels upward toward the air outlet after the bubbles and foam have been disrupted by the bubble barrier.

13. A saliva collector as in claim 1, wherein the air flow path travels laterally outward toward the air outlet after the bubbles and foam have been disrupted by the bubble barrier.

14. A saliva collector as in claim 1, wherein the air flow path travels laterally inward toward the bubble barrier prior to the bubbles and foam being disrupted by the bubble barrier.

15. A saliva collector as in claim 1, wherein the air flow path travels downward from the air inlet toward the bubble barrier prior to the bubbles and foam being disrupted by the bubble barrier.

16. A saliva collector as in claim 1, wherein the outer portion of the reservoir is open to the air inlet and the inner portion of the reservoir is open to the air outlet.

17. A saliva collector as in claim 1, wherein the air inlet is configured to draw the air stream from an oral appliance held at least partially in the patient's oral cavity with a bite structure of the oral appliance held between upper and lower teeth of the patient.

18. A saliva collector as in claim 1, wherein the top of the reservoir comprises a removable top, the removable top comprising the air inlet and the air outlet.

19. A saliva collector for attachment in a vacuum line which aspirates an air stream entrained with saliva, said saliva collector comprising:

a reservoir having a bottom, a top, and a sidewall which together define an interior volume, said reservoir further having an air inlet and an air outlet with an air flow path between the air inlet and the air outlet; and a bubble barrier positioned within the interior of the reservoir so that all air on the flow path passes therethrough, wherein the bubble barrier is positioned within the interior of the reservoir to separate the reservoir into an inner portion and an outer portion, the bubble barrier extending to the bottom of the reservoir and the air flow path crossing the inner and outer portions, wherein the bubble barrier is configured to disrupt bubbles and foam present in the air stream before such bubbles of foam can reach the air outlet such that the bubbles and foam coalesce and return to a liquid state to fall to the bottom of the reservoir away from the air inlet and the air outlet, and wherein the air flow path travels laterally outward toward the air outlet after the bubbles and foam have been disrupted by the bubble barrier.

20. A saliva collector for attachment in a vacuum line which aspirates an air stream entrained with saliva, said saliva collector comprising:

a reservoir having a bottom, a top, and a sidewall which together define an interior volume, said reservoir further having an air inlet and an air outlet with an air flow path between the air inlet and the air outlet; and a bubble barrier positioned within the interior of the reservoir so that all air on the flow path passes therethrough, wherein the bubble barrier is positioned within the interior of the reservoir to separate the reservoir into an inner portion and an outer portion, the bubble barrier extending to the bottom of the reservoir and the air flow path crossing the inner and outer portions, wherein the bubble barrier is configured to disrupt bubbles and foam present in the air stream before such bubbles of foam can reach the air outlet such that the bubbles and foam coalesce and return to a liquid state to fall to the bottom of the reservoir away from the air inlet and the air outlet, and wherein the air flow path travels laterally inwards toward the bubble barrier prior to the bubbles and foam being disrupted by the bubble barrier.

\* \* \* \* \*